United States Patent

Weiss et al.

Patent Number: 5,578,753
Date of Patent: Nov. 26, 1996

[54] HUMIDITY AND/OR TEMPERATURE CONTROL DEVICE

[75] Inventors: John Weiss, Mt. Sinai, N.Y.; Chwen C. Jean, Taipei, Taiwan

[73] Assignee: Micro Weiss Electronics, Inc., West Babylon, N.Y.

[21] Appl. No.: 450,957

[22] Filed: May 23, 1995

[51] Int. Cl.$^6$ ............... H02H 3/00; F24F 6/00; B01F 3/02; G01W 1/00
[52] U.S. Cl. ............ 73/335.02; 73/29.02; 307/34; 307/116; 62/209; 62/214; 219/494; 236/44
[58] Field of Search ............ 73/335.02, 335.05, 73/29.02, 29.05; 62/85, 176, 195, 209, 214, 216; 219/494; 392/501, 497; 307/34, 35, 116, 117; 236/10, 11, 44; 361/93

[56] References Cited

U.S. PATENT DOCUMENTS

| | | | |
|---|---|---|---|
| 4,029,937 | 6/1977 | Russell | 219/295 |
| 4,227,411 | 10/1980 | Abramovich | 73/336.5 |
| 4,259,565 | 3/1981 | Ogino et al. | 219/216 |
| 4,481,813 | 11/1984 | Tanei et al. | 73/336.3 |
| 4,703,886 | 11/1987 | Kirby | 236/44 E |
| 4,734,554 | 3/1988 | Tateda et al. | 219/10.55 B |
| 4,768,378 | 9/1988 | Ando et al. | 73/336.5 |
| 4,812,615 | 3/1989 | Manzoni | 219/209 |
| 4,862,950 | 9/1989 | Gribble et al. | 165/20 |
| 4,864,829 | 9/1989 | Manning et al. | 62/85 |
| 4,889,280 | 12/1989 | Grald et al. | 236/440 |
| 4,911,357 | 3/1990 | Kitamura | 236/44 E |
| 4,938,928 | 7/1990 | Koda et al. | 422/98 |
| 5,168,170 | 12/1992 | Hartig | 307/35 |
| 5,196,781 | 3/1993 | Jamieson et al. | 320/61 |
| 5,200,589 | 4/1993 | Kim | 219/10.55 B |
| 5,341,986 | 8/1994 | Galba et al. | 236/11 |
| 5,343,746 | 9/1994 | Choi et al. | 73/335.05 |
| 5,361,184 | 11/1994 | El-Sharkawi et al. | 361/93 |

*Primary Examiner*—Hezron E. Williams
*Assistant Examiner*—J. David Wiggins
*Attorney, Agent, or Firm*—Hoffmann & Baron

[57] ABSTRACT

A humidity control device includes a microcontroller, a variable impedance humidity sensing circuit and a zero crossing detector circuit. The humidity sensing circuit and zero crossing circuit are provided with an AC line voltage and both have outputs which are provided to the microcontroller. The humidity control device also includes a semiconductor switch circuit which switches the AC line voltage to an external electrical device, such as a dehumidifier or heater, at the zero crossing.

17 Claims, 6 Drawing Sheets

HUMIDITY AND/OR TEMPERATURE CONTROL DEVICE

BACKGROUND OF THE INVENTION

1. Field of the Invention

The present invention relates to humidity and/or temperature control devices, and more particularly relates to a humidity or temperature control device having low power requirements and improved reliability.

2. Description of the Prior Art

Humidity sensors and humidity detection devices are well known in the art. Humidity control devices are commonly used in microwave ovens, humidifiers, dehumidifiers and clothes dryers, and in various electronic devices to minimize condensation due to sudden changes in temperature.

As discussed in U.S. Pat. No. 4,481,813 to Tanei, et al., known methods of humidity detection include optical changes in light reflection or water absorption spectra, changes in resonant frequency of piezo-resonators, changes in capacitance or changes in electric resistance. However, the method utilizing optics requires a highly precise optical system which is relatively expensive for use in domestic appliances. The methods of humidity detection using piezo-resonators or detecting changes in capacitance are also not preferred methods since the associated electronic circuits tend to be fairly complex. Accordingly, the method of humidity detection based upon changes in resistance has become the most preferred due to the simplicity of the associated electronic circuit.

Generally, the control circuits that employ a resistive humidity sensor may be categorized as either an alternating current (AC) type or a direct current (DC) type, depending upon the power source for the humidity detection circuit. The humidity control circuits respond to changes in the resistance of the humidity sensor caused by changes in humidity. Most commonly used humidity sensors exhibit a negative coefficient response whereby resistance of the humidity sensor decreases with an increase of moisture absorbed into the sensor surface. However, sensors have also been developed which exhibit an increase in electrical resistance with an increase in humidity detected by the sensor, i.e., a positive coefficient.

In order to avoid the more complicated circuits associated with AC driven sensors, humidity sensors driven by direct current (DC) have been developed. For example, U.S. Pat. No. 4,481,813 to Tanei, et al. discloses a direct current (DC) type humidity sensor whose resistance decreases with an increase in humidity. The humidity sensor comprises a pair of counterposed electrodes, a humidity-sensitive layer of insulating porous metal oxide provided on and between the counterposed electrodes, and an organic polymer coating layer provided on the humidity-sensitive layer.

Yet another humidity sensor is disclosed in U.S. Pat. No. 4,938,928 to Koda, et al. This humidity sensor comprises a metal heat generating member formed with a heat-resistant insulating coating and an atmosphere-sensitive layer supported on the coating. At least one electrode is connected to the atmosphere-sensitive layer for detecting a combustible gas, humidity or the like.

The most common circuit for measuring and controlling humidity utilizes an integrated circuit which outputs a signal to a sensor. A return signal is responsive to a resistance or capacitance of the sensor circuit and this return signal is analyzed by a microprocessor to determine the relative humidity. Such a circuit is described in U.S. Pat. No. 5,200,589 to Kim.

The Kim patent discloses a microwave oven having a fan motor whose rotation is controlled based upon the relative humidity within the oven. A control circuit is utilized which comprises a microprocessor, a zero balance circuit, an absolute humidity sensor, a humidity detecting circuit and a relay driving circuit. More specifically, the control circuit compensates for the humidity that exists before the heating cycle in the microwave oven by zero balancing the humidity detecting circuit during the beginning stage of the cycle. The Kim patent also discloses using a zero crossing circuit coupled to the microprocessor to help phase control the fan motor of the oven. This is accomplished by triggering a phototriac at various phase angles to thus control the speed of the fan to thereby control the humidity of the oven cavity by controlling the exhaust.

Many conventional humidity sensors and circuits have several common disadvantages. One such disadvantage is that the power requirements to drive the circuits tend to be relatively high. Some conventional power control circuits employ a zero-crossing detector directly driving a phototriac. Such circuits may draw 30 milliamperes or more of current. Additionally, variations in line voltage may cause conventional humidity detection circuits to be inaccurate. It is also known that temperature changes may affect the resistance of the humidity sensor used in conventional circuits.

Conventional temperature control circuits also have a number of disadvantages. They are often required to switch on and off high power devices, such as heaters, which may consume 750 to 1500 watts of power at 110 volts AC. A heater may draw high currents over relative long stretches of house wiring every time it is energized by the temperature control circuit. The result is large voltage drops across the house wiring to which the heater is connected. Other electrical devices, such as lamps or lighting fixtures, connected to the same wiring as the heater, may be affected.

For example, when the heater is turned on by the temperature control circuit, lights may dim significantly. This continual dimming and brightening of lights every time the heater is cycled on and off is noticeable and disconcerting to occupants in the dwelling where the heater is being used. It is the abrupt transition from bright to dim to bright again that is so noticeable.

OBJECTS AND SUMMARY OF THE INVENTION

It is an object of the present invention to provide a humidity and/or temperature control device which overcomes the disadvantages of known devices.

It is another object of the present invention to provide a humidity control device which self-compensates for variations in line voltage.

It is yet a further object of the present invention to provide a microprocessor-controlled humidity control device including an AC resistive humidity sensor.

It is still a further object of the present invention to provide a humidity control device powered by AC line voltage for controlling a dehumidifier or the like and which generates minimal radio frequency interference (RFI).

It is yet another object of the present invention to provide a humidity control device having reduced power consumption.

It is a further object of the present invention to provide a humidity control device having improved operating reliability over a range of operating temperatures.

It is yet a further object of the present invention to provide a humidity control device for use in consumer and industrial appliances and, in particular, a refrigerator.

It is still a further object of this invention to provide a temperature control device adapted to control an electrical device, such as a heater, where the energization and deenergization of that electrical device is less discernible to occupants of the house or facility where the electrical device is situated.

In accordance with one form of the present invention, a humidity control device includes an electronic circuit mounted in a vented, protective housing envisioned to be installed by the manufacturer in a consumer or industrial appliance, such as a refrigerator, whose humidity is to controlled. The electronic circuit is preferably connected to household power, either 110 or 220 volts.

The electronic circuit of the humidity control device preferably includes a humidity sensing circuit. The humidity sensing circuit is driven by the AC line voltage, and includes a balanced comparator circuit comprising two matched resistance paths, each being coupled to a respective identical rectifier and filter circuit, and a comparator, the inputs of which are coupled to the outputs of the rectifier and filter circuits. One resistance path includes an AC resistive humidity sensor, whose resistance varies with the humidity in the air it senses.

The comparator, in effect, compares the rectified and filtered voltage drop in each resistance path and provides an output signal indicative of whether the voltage drop is greater in one path or the other. In effect, the path without the humidity sensor generates a predetermined reference voltage at one input of the comparator against which the voltage at the other input generated by the path having the humidity sensor is compared. When the humidity in the air changes, the resistance of the humidity sensor exposed to the air also changes, and so does the voltage on the corresponding comparator input. The output signal of the comparator will change in accordance with whether this voltage is above or below the reference voltage on the other comparator input. For example, if the humidity in the air is below a set point humidity corresponding to the reference voltage, the output of the comparator will be in a low logic state, and if the humidity is above the set point humidity, the output of the comparator will be in a high logic state, or vice versa.

An AC resistive type humidity sensor is preferably used. This type tends to be more accurate than the DC type. If the humidity sensor is operated with an AC voltage, it will not become polarized as with the DC type sensor, which polarization could affect the accuracy of the humidity measurement. Accordingly, the two resistance paths are operated using an AC, rather than a DC, voltage.

The accuracy of many humidity sensors is also affected by temperature changes. To compensate for temperature variations, a thermistor or other temperature compensating device may be placed in the resistance path providing the reference voltage. If the humidity sensor's measurement of humidity changes due to temperature fluctuations, the reference voltage at the comparator will also change correspondingly due to the temperature compensating device, so that the humidity sensing circuit is substantially insensitive to temperature variations.

Because the resistance paths are matched, and the same AC line voltage is provided to each path, the resistive and other components in each path are affected equally by variations in the line voltage and by temperature, so that the two paths, in effect, track each other. Thus, a relative comparison of voltage drops is made, not an absolute comparison of fixed voltages. In this way, the humidity sensing circuit self-compensates for changes in line voltage and temperature, and yet provides the benefits inherent with the use of AC resistive type humidity sensors.

The electronic circuit further includes a microcontroller, a zero crossing detector and a power switching circuit. The zero crossing detector senses the zero crossing of the AC line voltage, and provides an output signal to the microcontroller indicating the zero crossing. The switching circuit may include a triac which is situated in series with an external electrical device, such as a dehumidifier or compressor, to be controlled by the circuit.

In response to the output signal from the comparator, and in accordance with the zero crossing of the AC line voltage sensed by the zero crossing detector, the microcontroller generates an output signal which is provided to the switching circuit to energize or deenergize the electrical device connected to the switching circuit.

The electronic circuit of the humidity control device may be easily changed to control an electrical device in response to changes in temperature rather than humidity. The humidity sensor may be replaced with a thermistor or other device whose resistance changes with temperature. The microcontroller may be programmed to power up a heater, for example, in steps or gradations of power. For example, rather than providing a full 750 watts called for by the heater, the microcontroller of the temperature control device of the present invention may trigger the triac on for half cycles of the AC line voltage for a predetermined period of time. This would provide a transition of from 0 to only 375 watts, rather than to full power at 750 watts. Such a transition will cause a lower line voltage drop, and would be less discernible to occupants of the dwelling in which the heater is used, as lights in the dwelling connected to the same house wiring as the heater may not dim so significantly.

If, after the elapse of a predetermined period of time programmed in the microcontroller, the temperature control device determines that it is still necessary to maintain the heater on, the microcontroller will turn the triac on for full cycles of the AC line voltage. This transition will still only be equivalent to 375 watts of power, that is, from 375 watts to 750 watts. The transition to this higher power, as before, will be less discernible to an occupant than if full power is abruptly applied to the heater.

The microcontroller may be programmed to make smaller steps or gradations in powering up an electrical device, such as where full cycles are gradually interspersed with half cycles over a repetitive predetermined number of cycles of the AC line voltage until entirely full cycles of power are provided to the electrical device. In this way, the transition between no power and full power to the electrical device is not immediate but rather is gradual over time, and the application of power to the electrical device will not be as perceptible to an occupant of the dwelling in which the electrical device is used.

A preferred form of the humidity/temperature control device, as well as other embodiments, objects, features and advantages of this invention, will be apparent from the following detailed description of illustrative embodiments thereof, which is to be read in connection with the accompanying drawings.

DETAILED DESCRIPTION OF THE PREFERRED EMBODIMENTS

Figure 1:
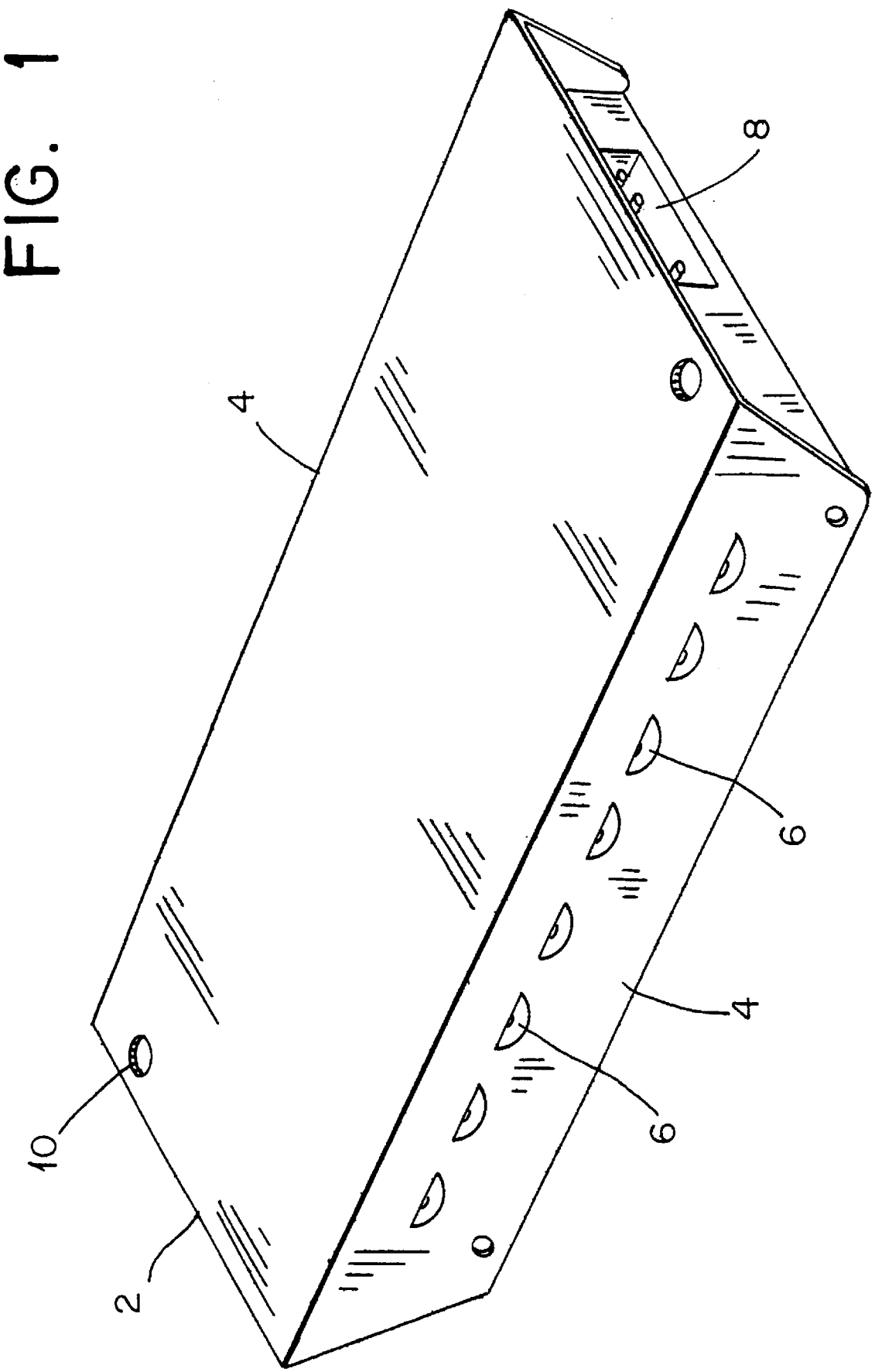
FIG. 1 is a perspective view of a housing for the humidity control device of the present invention.

Referring initially to FIG. 1 of the drawings, it will be seen that a humidity control device formed in accordance with one form of the present invention is particularly adapted for mounting to a wall or a housing of an appliance or other electrical device, such as a refrigerator. The humidity control device of the present invention includes a housing 2, preferably formed from sheet metal or molded plastic. The housing 2 includes sidewalls 4 having a plurality of openings 6 formed through the thickness of the housing. The openings 6 are provided so that convection currents of air may pass through the interior of the humidity control device defined by the housing 2. In this way, a humidity sensor, which is mounted with other electronic circuitry in the interior of the housing, will be exposed to ambient humidity conditions and will react accordingly.

The housing 2 of the humidity control device further includes an opening formed through the thickness thereof to expose a connection plug 8 for connecting the humidity control device to an AC power source. The connection plug 8 is mounted on a printed circuit board which also has mounted thereon the electronic circuit of the humidity control device of the present invention. The housing 2 also includes a pair of mounting holes 10 for mounting the humidity control device to a wall of an appliance or other electrical device.

Figure 2:
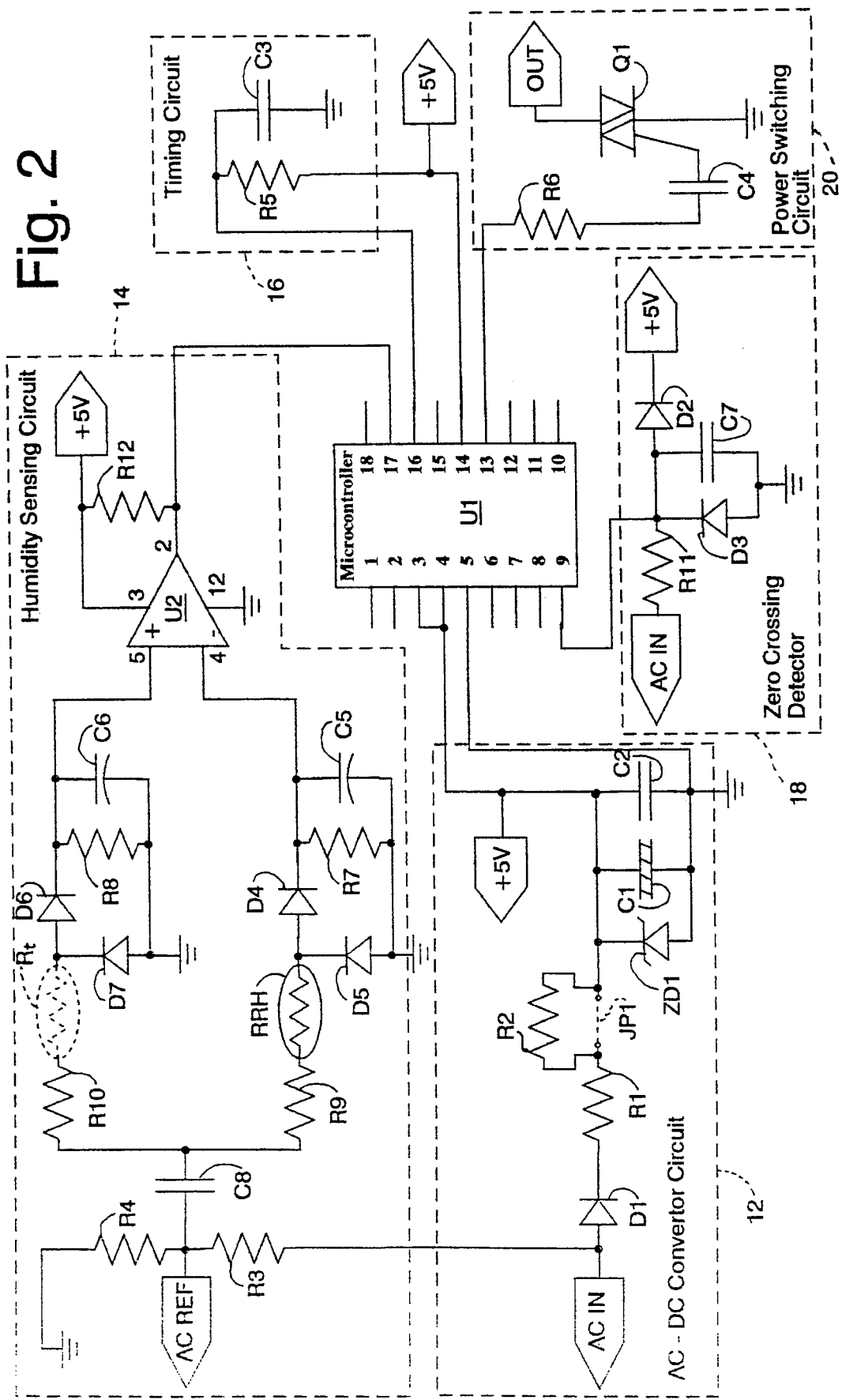
FIG. 2 is a schematic diagram of a preferred form of an electronic circuit used in the humidity control device of the present invention.

FIG. 2 is a schematic diagram of a preferred form of an electronic circuit forming a portion of the humidity control device of the present invention. The electronic circuit is designed to operate on a line voltage of either 110 or 220 volts AC. The electronic circuit for the humidity control device preferably operates to switch on a heater or dehumidifier if the humidity sensor detects an ambient humidity which is above a predetermined set point, for example, greater than 65% relative humidity. It is envisioned, however, that the humidity control device will work equally as well to add moisture to the air, such as by controlling a humidifier, when the sensed humidity in the air falls below the set point.

As shown in FIG. 2, the preferred electronic circuit of the present invention includes an AC-DC convertor circuit 12 for generating from the AC line voltage a regulated DC voltage for powering the electronic components of the circuit. The AC-DC convertor circuit 12 includes a half wave rectifier comprising diode D1, a voltage regulator comprising zener diode ZD1, and a filter circuit comprising parallelly connected electrolytic and ceramic capacitors, C1 and C2, respectively.

More specifically, AC line voltage ("AC IN", FIG. 2) is received through the connector 8 and provided to the anode of diode D1, whose cathode is connected to a voltage limiting resistor R1. The other end of resistor R1 is coupled to the cathode of zener diode ZD1 through a jumper wire, JP1, if a line voltage of 110 volts AC is used. The anode of zener diode ZD1 is grounded. Jumper wire JP1 is in parallel with, and thus shorts out, another voltage limiting resistor R2. If 220 volts AC is used, jumper wire JP1 is removed so that resistors R1 and R2 are in series, to drop further the AC line voltage.

Zener diode ZD1 is preferably a 4.7 volt zener, which provides regulation to the half wave rectified voltage from diode D1. Capacitors C1 and C2 are coupled in parallel with zener diode ZD1 to filter the regulated voltage and provide, preferably, a 5 volt DC voltage ("+5 V", FIG. 2) to the electronic components of the circuit.

The electronic circuit of the present invention also includes a humidity sensing circuit 14. As will be explained, the humidity sensing circuit 14 operates from the AC line voltage provided to the humidity control device, and is self-compensating for line voltage and temperature changes.

As shown in FIG. 2, the AC line voltage is reduced through a voltage divider circuit (i.e., a resistor divider network) comprising series-interconnected resistors R3 and R4 to provide a reference AC voltage ("AC REF", FIG. 2) at the juncture of the resistors. It is preferred that the reference voltage be about 1 volt (in the case of 110 volt AC line voltage). This AC reference voltage is provided to two resistive legs of a comparator circuit through AC coupling capacitor C8. One resistive leg includes resistor R10, while the other resistive leg includes resistor R9 in series with an AC resistive type humidity sensor RRH. The value of resistor R9 is chosen based upon the resistive characteristics of the humidity sensor RRH at a given temperature and humidity such that the sum of the resistances of resistor R9 and sensor RRH in the one leg equals that of resistor R10 in the other leg.

Each of resistors R9 and R10 is shown in FIG. 2 as a fixed resistor. However, it should be realized that resistors R9 and R10 may be variable resistors, to adjust the reference voltage (i.e., the humidity set point) by resistor R10 and to trim resistor R9 so that the total resistances of the components in each resistive leg are matched.

Many humidity sensors are affected by temperature, and their humidity measurement at a given humidity will thus change as the temperature changes. To compensate for this effect, the humidity circuit 14 may include a thermistor or other temperature compensating device $R_T$ (shown in phantom), whose resistance varies with temperature in the same manner as does the resistance of the humidity sensor RRH varies with temperature. If such a temperature compensating device $R_T$ is used, it may be placed in series with resistor R10 in the reference voltage resistive leg, as shown in FIG. 2. Alternatively, a temperature compensating device having resistance/temperature characteristics that are inversely proportional to those of humidity sensor RRH may be positioned in series with sensor RRH in its respective resistive leg. In any event, if such a temperature compensating device $R_T$ is used, the total resistance of one resistive leg is still made substantially equal to that of the other resistive leg. In order to simplify the description of the circuit which follows, it will be assumed that the temperature compensating device $R_T$ is not included.

Each resistive leg also includes a half wave rectifier and filter circuit, preferably using identical components. More specifically, one end of resistor R10 is coupled to the anode of diode D6, whose cathode is coupled to the parallel combination of resistor R8 and capacitor C6, whose other ends are grounded, and to the non-inverting input ("+") of comparator U2. Similarly, the series connection of resistor R9 and humidity sensor RRH is coupled to the anode of diode D4, whose cathode is connected to resistor R7 and to capacitor C5 (whose other ends are also grounded) and to the inverting input ("−") of comparator U2.

Thus, the humidity sensor RRH is exposed to an AC voltage, as is resistor R10 in the other leg, and the AC voltages are rectified by diodes D4 and D6 and filtered by capacitors C5 and C6 so that a DC voltage is provided to the inputs of the comparator U2. Because the sensor is exposed to an AC voltage, it will not become polarized and its accuracy will not be affected, and yet a comparison of the voltages on the two resistive legs is made with DC voltages.

Resistors R8 and R7 respectively form a voltage divider with resistor R10 and the series combination of resistor R9 and sensor RRH. Resistors R7 and R8 are provided to attenuate further the DC voltages seen at the inputs of the comparator U2. Also, diodes D5 and D7 are included and are respectively connected between the anodes of diodes D4 and D6 and ground. Diodes D5 and D7 are provided to clip the negative swing of the AC voltage in each leg so that the DC voltages applied to the comparator inputs do not fall substantially below ground.

Each component of the first resistive leg (including the rectifier and filter circuit), that is, diodes D4 and D5, resistor R7 and capacitor C5, is preferably identical to those of the second resistive leg, that is, diodes D6 and D7, resistor R8 and capacitor C6, respectively, and, as mentioned previously, resistor R10 is comparable in resistance to that of the combination of resistor R9 and sensor RRH, so that the two resistive legs are comparably matched. Accordingly, should the resistance of any of the components in one leg change due to temperature, the resistances in the other leg will change comparably and the two legs will track each other. The optional temperature compensating device $R_T$ may be used to provide temperature compensation for humidity sensor RRH. Thus, the voltages at the comparator inputs relative to each other will remain constant although the absolute voltages may change with temperature or with variations in line voltage.

The comparator U2 is preferably a quad comparator integrated circuit, such as Part No. LM339, or its equivalent, manufactured by many companies, such as Signetics Corporation in Sunnyvale, Calif. Since the output stage of the comparator is an open collector circuit, a pull-up resistor R12 connected to 5 volts is used.

The reference voltage on the non-inverting input of comparator U2 is chosen by selecting resistor R10 with a certain resistance. This reference voltage corresponds to a desired humidity set point, for example, 65%, above which the humidity control circuit is to turn on a heater or dehumidifier to reduce the humidity. Resistor R9 is chosen, in combination with sensor RRH, to match the resistance of resistor R10.

If the ambient humidity detected by sensor RRH falls below the humidity set point, the resistance of sensor RRH increases and the voltage dropped across resistor R7 and provided to the inverting input of the comparator U2 decreases below the reference voltage provided on the non-inverting input. The comparator U2 will generate an output signal having a logic one state. If the humidity increases above the set point, the resistance of sensor RRH decreases, which correspondingly increases the voltage on the inverting input such that it is above the reference voltage. Under these conditions, the comparator U2 will generate an output signal having a logic zero state.

The electronic circuit of the humidity control device further includes a microcontroller U1, a timing circuit 16 for the microcontroller U1, a zero crossing detector 18 and a power switching circuit 20, which is used to selectively energize or deenergize a particular external electrical device, such as a heater or dehumidifier.

The zero crossing detector 18 receives the AC line voltage ("AC IN") and includes resistor R11, one end of which is provided with the AC line voltage, diode D3, having its anode grounded and its cathode coupled to the other end of resistor R11, capacitor C7 connected in parallel with diode D3, and a diode D2, whose anode is connected to resistor R11 and on whose cathode is provided 5 volts.

More specifically, the 110 volt AC line voltage is provided to the zero crossing detector through an isolation resistor R11 of relatively high resistance. Diode D2 (connected to 5 volts) and diode D3 respectively clip the line voltage at approximately +4.3 volts (i.e., +5 volts−the 0.7 volt drop across diode D2) and substantially ground (i.e., −0.7 volts, the voltage drop across diode D3). This dual clipping action squares the signal and limits its swing, as mentioned above, to between approximately ground and +5 volts, thus creating a pulsed output signal whose leading and trailing edges substantially coincide with the zero crossing of the AC line voltage provided to the humidity control device and to the heater, dehumidifier or the like controlled by the device. This pulsed output signal is provided to the microcontroller U1. Capacitor C7, in conjunction with resistor R11, provides filtering.

The microcontroller U1 is preferably Part No. PIC16C54 manufactured by Microchip Technology Inc. of Chandler, Ariz., although other microprocessors or microcontrollers are suitable for use. An external timing circuit 16 comprising resistor R5 connected to +5 volts and capacitor C3 connected between resistor R5 and ground is connected to the oscillator input (Pin 16) of the microcontroller U1 and controls the rate of the internal clock to about 500 kHz.

The microcontroller U1 receives the output signals from the zero crossing detector 18 and the comparator U2 and, in response, generates an output signal which is provided to the power switching circuit 20.

More specifically, the output signal from microcontroller U1 is provided through the series connection of resistor R6 and capacitor C4 of the power switching circuit 20 to the gate of a triac Q1. One terminal of triac Q1 is grounded, and the other terminal is provided to the other wire of the AC power line ("OUT", FIG. 2) through connector 8, which line goes to the electrical device, such as a heater or dehumidifier, to be controlled by the power switching circuit 20. The microcontroller U1 triggers the triac Q1 on and off at the zero crossing of the AC power line to selectively energize and deenergize the electrical device controlled by the humidity control device of the present invention.

Because it is envisioned that high power electrical devices, such as heaters, dehumidifiers or condensers, are to be controlled by the humidity control device, energizing and deenergizing such devices at the zero crossing of the AC power reduces radio frequency interference (RFI), as is well known in the art.

A parts list for the circuit illustrated in FIG. 2 is provided below. Also, the pin numbers shown in FIG. 2 for the microcontroller U1 and comparator U2 relate to the parts specified in the list, although it is envisioned that components comparable to those listed below, connected differently from that shown in FIG. 2, may be suitable to achieve the same results.

PARTS LIST FOR CIRCUIT SHOWN IN FIG. 2

| Part Description | Reference Designation |
|---|---|
| Resistor 18KΩ | R1 |
| Resistor 18KΩ | R2 |
| Resistor 0.5MΩ | R3 |
| Resistor 5.6KΩ | R4 |
| Resistor 5.6KΩ | R5 |
| Resistor 100Ω | R6 |
| Resistor 100KΩ | R7 |
| Resistor 100KΩ | R8 |
| Resistor 1KΩ | R9 |
| Resistor 32KΩ | R10 |
| Resistor 2MΩ | R11 |
| Resistor 5.1KΩ | R12 |
| Diode 1N3804 | D1 |
| Diode 1N4148 | D2 |
| Diode 1N4148 | D3 |
| Diode 1N4148 | D4 |
| Diode 1N4148 | D5 |
| Diode 1N4148 | D6 |
| Diode 1N4148 | D7 |
| Zener Diode MTZ4.7 4.7V | ZD1 |
| Capacitor 20 μF | C1 |
| Capacitor .1 μF | C2 |
| Capacitor 30 pF | C3 |
| Capacitor .1 μF | C4 |
| Capacitor 10 μF | C5 |
| Capacitor 10 μF | C6 |
| Capacitor .01 μF | C7 |
| Capacitor .1 μF | C8 |
| Triac BT136, 500E (p9328) | Q1 |
| Microcontroller, PIC 16C54 | U1 |
| Comparator, LM339 | U2 |

Figure 3:
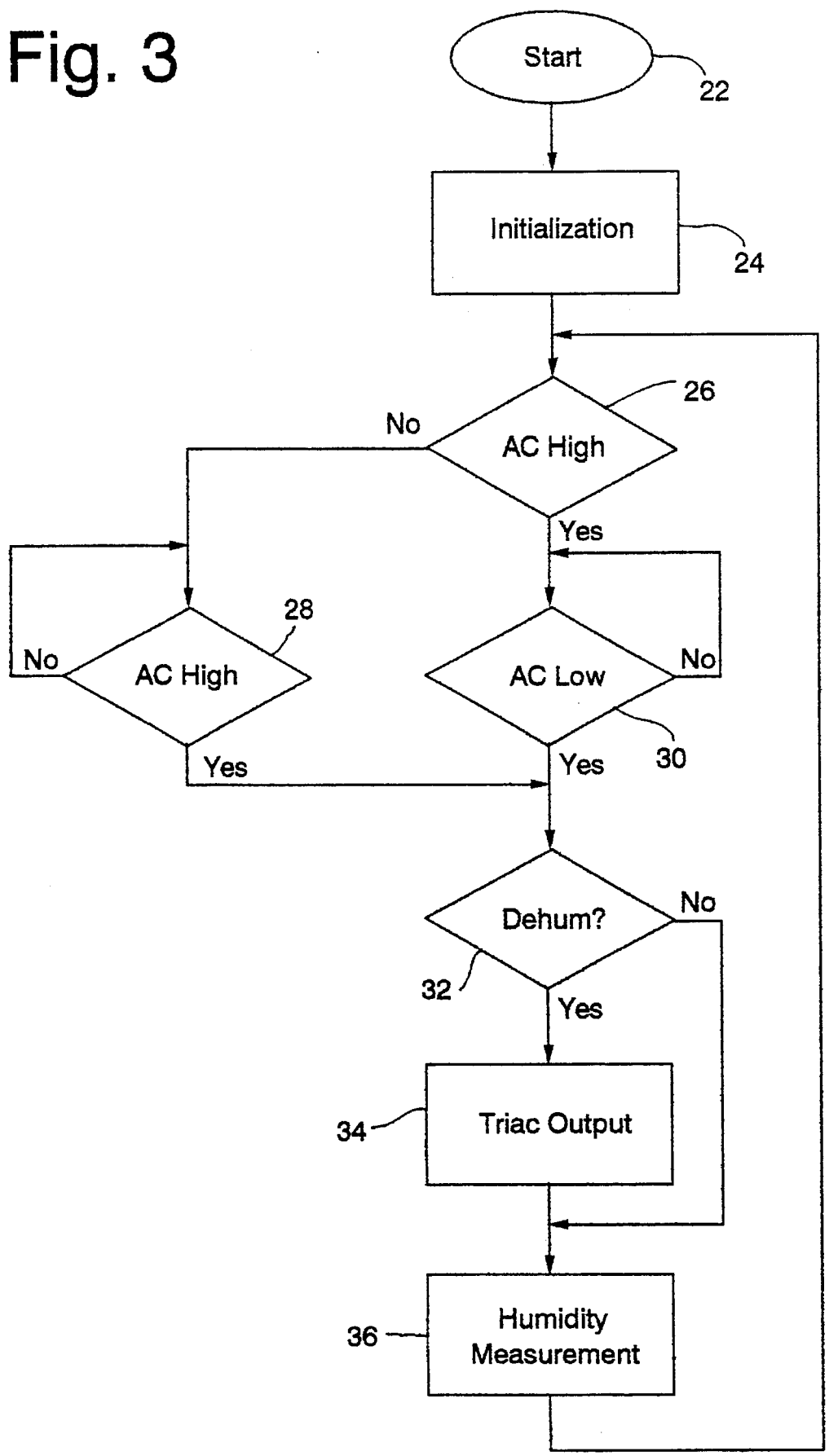
FIG. 3 is a flow chart of the operation of the humidity control device of the present invention.

Referring now to FIG. 3, a flow chart of the operation of the humidity control device of the present invention is shown. After power is provided to the humidity control device, the microcontroller U1 is powered up and an operational routine starts (Block 22). The microcontroller U1 then goes through an initialization routine (Block 24). After completion of the initialization routine, the humidity control device is ready for operation.

Next, the microcontroller U1, in association with the zero crossing detector 18, determines the zero crossing of the AC line voltage. More specifically, the microcontroller U1 determines from the pulsed output signal from the zero crossing detector 18 if the AC line voltage is in the positive portion of its cycle, with respect to ground, in other words, whether the pulsed output signal from the zero crossing detector is in a high logic state (Block 26). If it is not, then the operational routine goes into an endless loop until this high logic state is detected (Block 28).

If the pulsed output signal from the zero crossing detector is not high (Block 26), then the microcontroller determines if the AC line voltage is in the negative portion (with respect to ground) of its swing, in other words, whether the pulsed output signal from the zero crossing detector 18 is in a low logic state (Block 30). The routine stays in this endless loop (Block 30) until a low is detected. It should be noted that the operational routine illustrated by Blocks 26–30 will detect the transition between the high and low logic states of the pulsed output signal from the zero crossing detector 18, which transition coincides with the zero crossing of the AC line voltage.

If such a transition is detected, the operational routine of the humidity control device will next determine if dehumidification is necessary or not (Block 32). The microcontroller U1 looks to the output signal from comparator U2 of the humidity sensing circuit (or to data stored in the microcontroller memory corresponding to the comparator output signal), which is indicative of whether the relative ambient humidity is above or below the humidity set point (Block 32). If dehumidification is required, the microcontroller U1 will trigger the triac Q1 on at the zero crossing of the AC line voltage for a predetermined period of time or until the humidity has decreased to below the set point (Block 34).

A humidity measurement (i.e., whether the humidity is above or below the set point) is then taken by the microcontroller U1 by looking at the output signal of the comparator U2, and this measurement is stored in the memory of the microcontroller U1 for reference in the next cycle of the routine (Block 36). This operational routine then returns to Blocks 26–30 to determine if a zero crossing has occurred.

As mentioned previously, the microcontroller U1 may keep the triac Q1 on for a predetermined period of time to maintain power to the dehumidifier or the like, even if the humidity has fallen below the set point. Similarly, the microcontroller may prevent the triac from triggering on if a second predetermined period of time after the last deenergization of the dehumidifier has not elapsed, even though the humidity has risen above the set point. The purpose of these time periods is to prevent overcycling the condenser, motor or other component of the dehumidifier or the like to prevent damage to the component. The time periods may be programmed into the microcontroller U2.

Chart I below is a preferred source code program for the operation of the microcontroller U1, written using the op code of the particular microcontroller mentioned previously, Part No. PIC16C54 manufactured by Microchip Technologies Inc.:

CHART I
PROGRAM FOR MICROCONTROLLER

```
;********EQU DEFINE********
RTCC       EQU    1       Fos=4MHz, 0.30mS—>256.4*.25*32=32uS
RA         EQU    5
RB         EQU    6
STATE      EQU    0DH
;****************************************************************************
;7         6          5           4             3             2        1          0
;          TESTING    TESTMODE    WRITE TIMER   LIGHT/BLACK             OUTPUT     HIGH/LOW
;****************************************************************************
HUM_H      EQU    10H
HUM_L      EQU    12H
```

CHART I
PROGRAM FOR MICROCONTROLLER

```
PULSWID     EQU         03H
HUMCOUNT    EQU         OFH
;**********************************************************************
            ORG         1PFH
            GOTO        START
;**********************************************************************
            ORG         OOH
START       NOP
            MOVLW       PULSWID
            OPTION
            CALL        DELAYY
            MOVLW       03H
            TRIS                    RA
            MOVLW       OPH
            TRIS                    RB
            CALL        DELAYY
            CLRF                    STATE
;*******************test start****************************************
CHK_AC      CLRF                    RB
            BTFSS       STATE, 1
            BSF                     RB,4
            CLRF                    HUM_L
            MOVLW       HUMCOUNT
            MOVWF                   HUM_H
            BTFSS       RB,3                    ;AC is high?
            GOTO                    AC_LOW
AC_HIGH     BTFSC       RB,3                    ;AC is low?
            GOTO                    AC_HIGH
            BTFSS       STATE,1
            GOTO                    HUM_TEST
            BSF                     RB,4
            CALL        DELAY_1
            CALL                    OUT_10
            GOTO                    HUM_TEST
;**********************************************************************
AC_LOW      BTFSS       RB,3                    ;AC is high?
            GOTO                    AC_LOW
            BTFSS       STATE,1
            GOTO                    HUM_TEST
            BCF                     RB,4
            CALL                    OUT_10
            GOTO                    HUM_TEST
;**********************************************************************
HUM_TEST    BTFSS       RA,0
            GOTO                    D_HUM       ;HUM>65%
            CALL        DELAY_1                 ;DELAY 1mS
            DECFSZ                  HUM_H       ;TEST TIME COUNT
            GOTO                    HUM_TEST
RCHK_AC     CLRF                    STATE
            GOTO                    CHK_AC
;**********************************************************************
D_HUM       CALL                    DELAY_1
            INCF                    HUM_L
H_HUM       DECFSZ                  HUM_H
            GOTO                    HUM_1
            MOVLW       5
            SUBWF       HUM_L,O
            SKPC
            GOTO        RCHK_AC
            MOVLW       10H
            SUBWF       HUM_L
            SKPNC
            GOTO                    RCHK_AC
            BSF                     STATE,1
            GOTO                    CHK_AC
;**********************************************************************
HUM_1       BTFSS       RA,0
            GOTO                    D_HUM
            CALL        DELAY_1
            DECF                    HUM_L
            GOTO                    H_HUM
;**********************************************************************
DELAYY      CLRF                    RTCC
DELAY10     CLRWDT
            MOVLW       .31
            XORWF       RTCC,0
            SKPZ
```

CHART I
PROGRAM FOR MICROCONTROLLER

```
         GOTO              DELAY10
         RETLW    00H
;****************************************************************
DELAY_0  CLRF              RTCC
         NOP
LOOP0    DECFSZ            RTCC,0
         GOTO              LOOP0
         RETLW    00H
;****************************************************************
DELAY_1  CLRF              RTCC
         CLRWDT
LOOP1    MOVLW    0AH
         XORWF    RTCC,0
         SKPZ
         GOTO              LOOP1
         RETLW    00H
;****************************************************************
```

Figure 4:
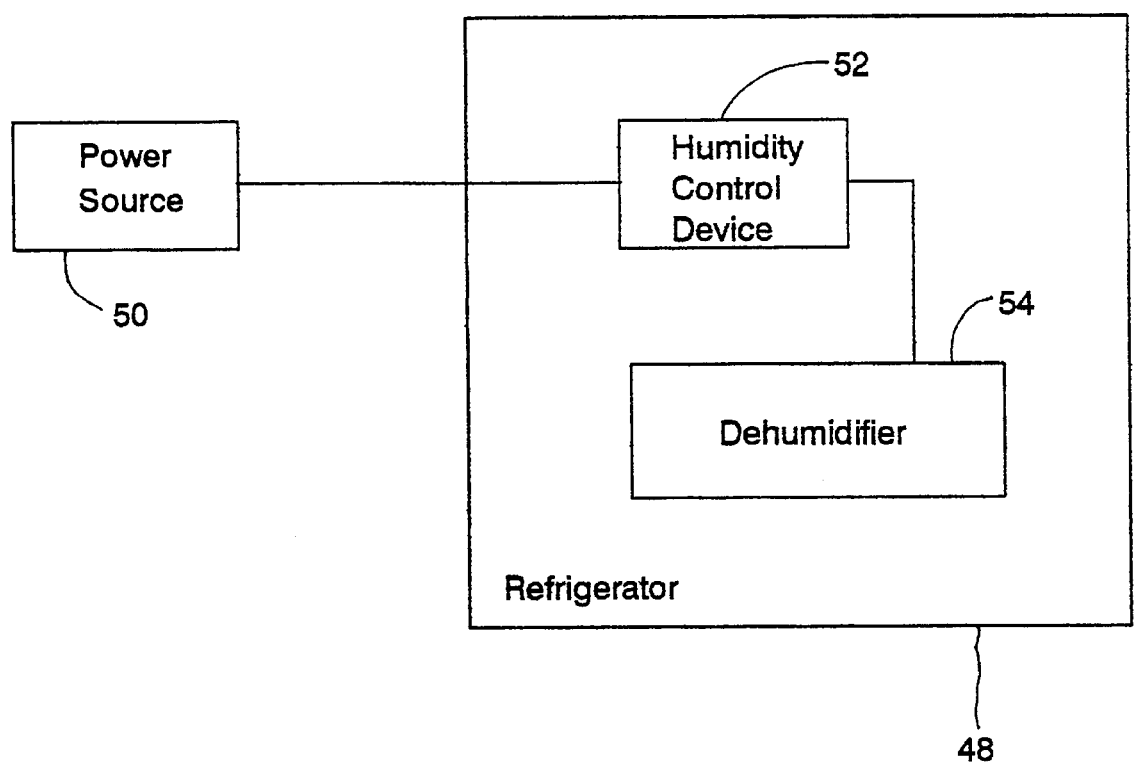
FIG. 4 is a block diagram of an appliance envisioned to incorporate the humidity control device of the present invention.

FIG. 4 is a block diagram illustrating the use of the humidity control device of the present invention, in one of many appliances, namely, a refrigerator 48. The refrigerator 48 is coupled to a power source 50, such as an AC line voltage of 110 volts. The line voltage is also applied to the humidity control device 52 formed in accordance with the present invention which is mounted within the refrigerator 48. Depending upon a determination of the relative humidity by the humidity control device 52, a dehumidifier 54 is cycled on and off to maintain the relative humidity inside the refrigerator to below a set point fixed by the humidity control device. The dehumidifier 54 may be in the form of a compressor or heater forming part of the refrigerator 48.

The humidity control device formed in accordance with the present invention advantageously uses a microprocessor to control selectively the energization of an external electrical device. The power consumption of the humidity control device is minimal, that is, approximately 0.3 watts. The AC resistive type humidity sensor RRH is operated from the AC line voltage and, hence, no polarization of the sensor occurs, and the control device remains accurate over years of use. The matched resistive legs of the humidity sensing circuit 14 further improves the accuracy of the control device by self-compensating for any AC power line variations. The power switching circuit 20 energizes and deenergizes the dehumidifier or the like at the zero crossing of the AC line voltage, thereby reducing radio frequency interference (RFI). The low power requirements allow for a simple, solid state power control of an external electrical device.

It should be noted further that the microcontroller U1 requires only two input signals to provide a programmed control of the triac Q1, which are the output signals from the comparator U2 and the zero crossing detector circuit 18. This leads to an uncomplicated circuit for the humidity control device, and low power requirements, and yet provides a programmed control of the external electrical device, which is not provided with conventional power control devices where the zero crossing detector directly controls a phototriac or the like.

It will be appreciated by those skilled in the art that the humidity control device of the present invention may be used to operate either a humidifier or a dehumidifier, depending upon the specific application. The humidity control device may be used in conjunction with many appliances and electrical devices in which it is beneficial to control humidity, and is not limited to those specific embodiments described herein.

The humidity control device described previously may be easily changed to function as a temperature control device to control a heater, for example. The humidity sensor RRH (FIG. 2) may be replaced by a thermistor or other component whose resistance varies with temperature. The comparator U2 would function in the same manner as it did in the humidity control device by providing an output signal which is indicative of whether the ambient temperature sensed by the thermistor (in place of humidity sensor RRH) and corresponding to the signal provided to the inverting input of comparator U2 is above or below a set point temperature set by resistor R10 and corresponding reference voltage provided to the non-inverting input of comparator U2.

For the temperature control device of the present invention, the microcontroller U1 may be specifically programmed to power up the heater or other external electrical device in steps or gradations. For example, when the microcontroller U1 receives a signal from the comparator U2 indicating that the ambient temperature has fallen below the temperature set point, the microcontroller may be programmed to provide half cycles of power to the heater by triggering the triac Q1 on for half cycles of the AC line voltage at each zero crossing of the AC line voltage. The half cycle power continues for a predetermined period of time which is programmed into the microcontroller, after which time the microcontroller triggers the triac Q1 on for full cycles of the AC line voltage at the zero crossing of the voltage. This is an example of a two step powering up of the heater or other electrical device by the temperature control device of the present invention.

To minimize the perceptibility of the deenergization of the heater (as well as its energization), the microcontroller U1 may be programmed to power down the heater in steps or gradations in the same manner as it powers up the heater. For example, when the comparator U2 signals the microcontroller U1 that the ambient temperature has risen above the set point temperature, the microcontroller may be programmed to trigger the triac Q1 on only for half cycles (from full cycles) of the AC line voltage for a predetermined period of time, which time is programmed into the microcontroller memory. After the predetermined period of time has elapsed, the microcontroller U1 will turn off the triac Q1 completely. This is an example of a two step powering down of the heater or other external electrical device by the temperature control device of the present invention.

The microcontroller may also be programmed to make smaller steps or gradations in powering up the heater or other electrical device, such as where full cycles are gradually interspersed with half cycles over a repetitive predetermined number of cycles of the AC line voltage until entirely full cycles of power are provided to the electrical device. For example, a predetermined number of cycles, such as 60 cycles, is programmed into the microcontroller memory. The microcontroller will count the cycles of the AC line voltage and make a determination every time this block of 60 cycles has elapsed.

During the first 60 cycles, the triac Q1 is triggered on for only a half cycle at the 30th cycle in the first block. In the second block of 60 cycles, the triac is triggered on for half cycles at the 30th and 60th cycle of the block. In the third block of 60 cycles, the triac is triggered on at the 15th, 30th, 45th and 60th cycle, but only for half cycles. With each new block of 60 cycles, the microcontroller U1 divides the block into smaller steps, as described previously, and triggers the triac Q1 on for a half cycle once during each smaller step. This process continues until the triac is turned on for a half cycle every cycle of the 60 cycle block. Thus, half power is now being applied every cycle of the block of cycles.

The microcontroller now intersperses full cycles with the half cycles, and does this in the same manner as it did before for the half cycles. For example, in the next block of 60 cycles, the microcontroller U1 will trigger the triac Q1 on for a full cycle at the 30th cycle of the block. During the next block of cycles, the triac will be turned on for a full cycle at the 30th and 60th cycle. For the subsequent block of cycles, the microcontroller will trigger the triac on for full cycles only at the 15th, 30th, 45th and 60th cycle in that block. The triac will only be turned on for half cycles during the remaining cycles of each of those blocks. The microcontroller continually divides each subsequent block of cycles into smaller steps and periodically intersperses full cycles with the half cycles at each step in the block until the triac is turned on for full cycles every cycle of the block. At this point, full power is now being provided to the heater or other electrical device by the temperature control device of the present invention. The transition from no power to full power is gradually made over a number of cycles and is less perceptible to an occupant of the dwelling in which the heater or other electrical device is being used.

Powering down the heater is performed in the reverse manner by the microcontroller U1, that is, by periodically changing in each block of cycles a particular full cycle to a half cycle, successively, until the triac Q1 is completely turned off by the microcontroller U1.

Figure 5:
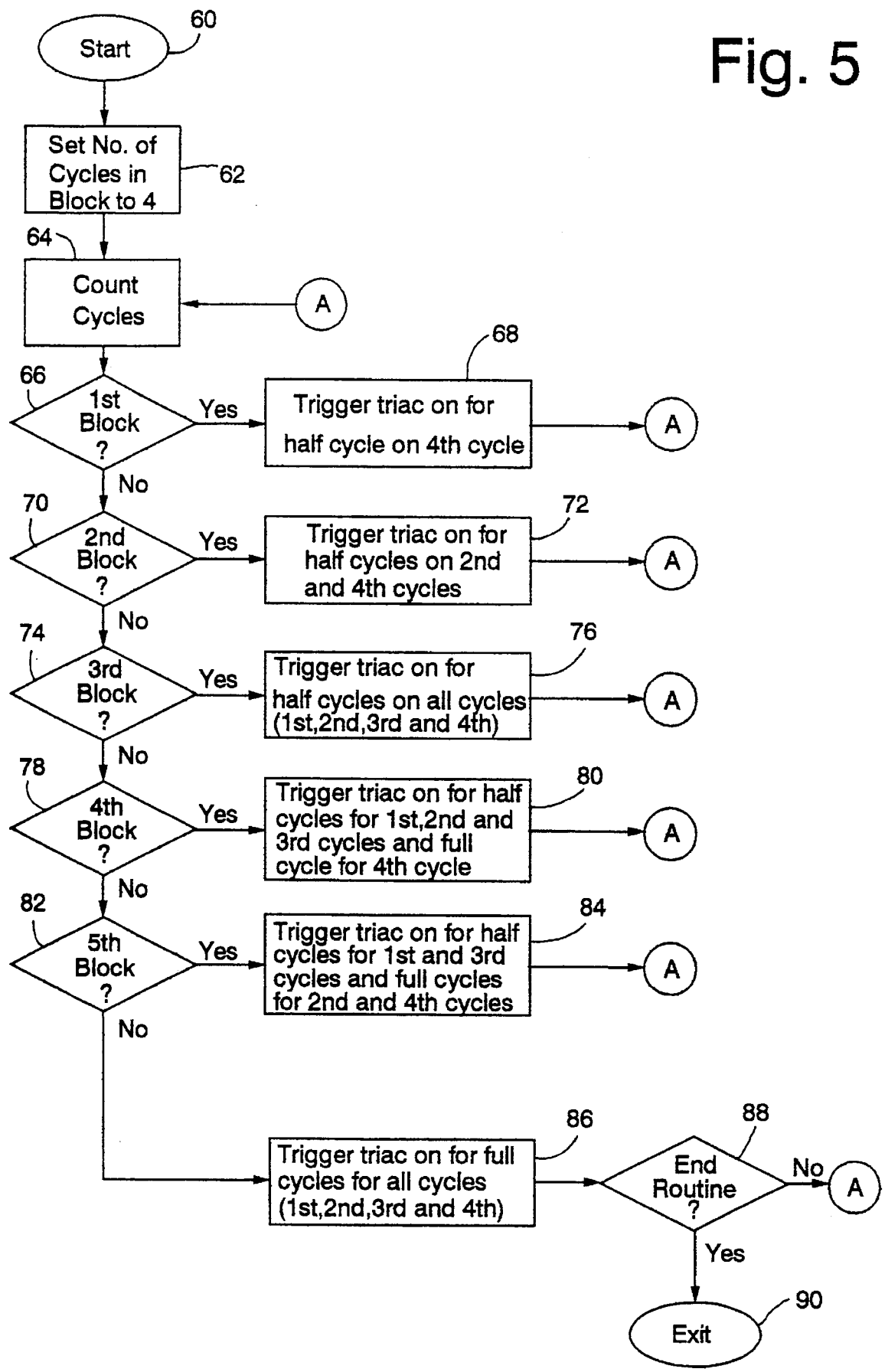
FIG. 5 is a flow chart of the operation of a temperature control device formed in accordance with the present invention.

FIG. 5 is a flow chart of a simplified operational routine for the microcontroller U1 illustrating how the microcontroller can power up a heater or other electrical device in a series of steps.

When the comparator U2 signals the microcontroller U1 that the heater should be turned on, the microcontroller goes into an operational routine (Block 60) which powers up the heater gradually in a series of steps. FIG. 5 is just one example of such a routine.

The microcontroller will set the number of cycles in the block of cycles (Block 62). In the example of the routine illustrated by FIG. 5, to simplify the explanation of the routine, the number of cycles in the block is set to four.

The microcontroller will count the number of cycles of the AC line voltage (Block 64), and obtains this information from the zero crossing detector circuit 18. In this way, the microcontroller U1 can tell when one block of cycles ends and the next one begins.

In the routine shown in FIG. 5, the microcontroller U1 determines from counting the cycles if a first block of four cycles of the AC line voltage is occurring (Block 66). If the count is within the first block, then the microcontroller will trigger the triac Q1 on for a half cycle on the fourth cycle of the first block of cycles (Block 68). The routine will then return to the microcontroller counting the cycles (Block 64). If the microcontroller determines that the next, second block of cycles of AC line voltage is occurring (Block 70), it will trigger the triac on for half cycles on the second and fourth cycles of this second block of cycles (Block 72), and return to counting the cycles of the AC line voltage (Block 64).

If the third block of cycles is occurring (Block 74), the microcontroller U1 will trigger the triac Q1 on for half cycles on all of the cycles of the third block (i.e., the first, second, third and fourth cycles). Now, half power is being applied to the heater or external electrical device by the temperature control device.

If the microcontroller determines that the subsequent fourth block of cycles is occurring (Block 78), the microcontroller will trigger the triac on for half cycles for the first, second and third cycles of the fourth block and for a full cycle during the fourth cycle of the fourth block (Block 80).

If the fifth block of cycles is occurring (Block 82), the triac will be triggered on for half cycles during the first and third cycles of the fifth block and for full cycles during the second and fourth cycles of the fifth block of cycles (Block 84).

For all subsequent cycles after the fifth block of cycles (Block 82), the microcontroller U1 will trigger the triac on for full cycles for all cycles (Block 86). Now, full power is being applied to the heater by the temperature control device of the present invention.

The microcontroller, based at least partially on the output signal from the comparator U2, will determine whether the powering up routine should be exited (Block 88), and if so, will exit the routine (Block 90).

The flow chart shown in FIG. 5 is an example where only four cycles are assigned to each block of cycles, and the half cycles and full cycles of power applied to the heater are spaced in time in each block of cycles so that the heater is powered up gradually over a number of cycles. Only four cycles were chosen per block to simplify the explanation of the routine; however, it is envisioned that many more cycles may be assigned to each block of cycles so that the external electrical device may be powered up in smaller steps more gradually over a longer period of time.

Also, the reverse routine may be used to powering down the heater by the temperature control device, the steps of which routine would be evident from the flow chart illustrated by FIG. 5 of the drawings.

Figure 6A:
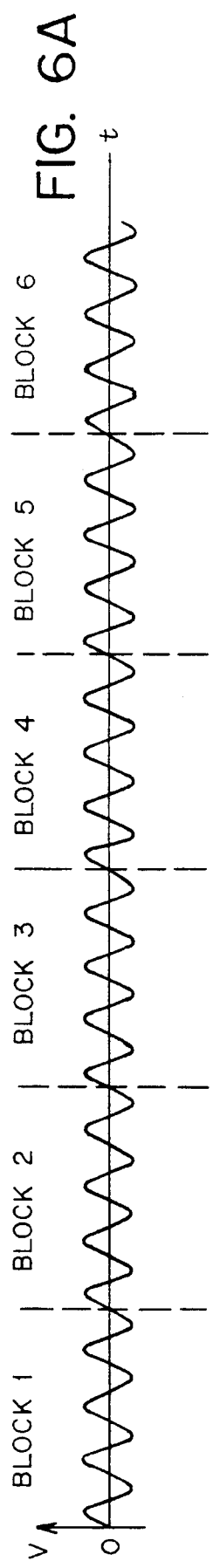
FIGS. 6A, 6B and 6C are graphs of voltage versus time depicting cycles of the AC line voltage and signals generated by the electronic circuit of the temperature control device of the present invention.

The blocks of cycles of the AC line voltage described previously in relation to the flow chart of FIG. 5 are shown in FIG. 6A. Four cycles of the AC line voltage are assigned to each block, and six blocks of cycles are shown.

Figure 6B:
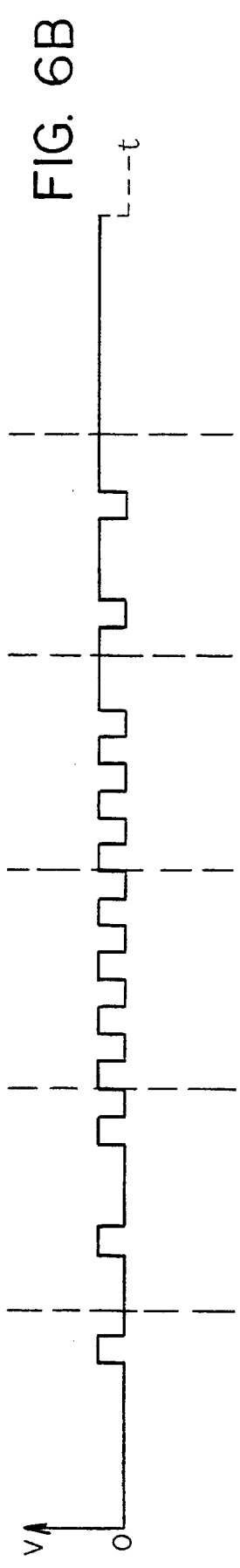

In alignment with FIG. 6A is shown in FIG. 6B the waveform of the output signal from the microcontroller U1 provided to the power switching circuit 20, including triac Q1, for the example given in the flow chart of FIG. 5. As can be seen from FIGS. 6A and 6B, for the first block of cycles (Block 1), a single half cycle pulse is generated, and the occurrence of the pulse, as with the pulses that follow, is timed to cause the triac Q1 to switch power to the electrical device at the zero crossing of the AC line voltage.

For the second block of cycles (Block 2), two half cycle pulses are generated by the microcontroller U1 to trigger triac Q1 on. For the third block of cycles (Block 3), a half cycle pulse is generated for each cycle of the AC line voltage. Thus, half power is now being applied to the electrical device controlled by the microcontroller firing the triac Q1.

The fourth block of cycles (Block 4) contains three half cycle pulses and one interspersed full cycle pulse from microcontroller U1 to triac Q1. The fifth block of cycles (Block 5) has two one half cycle pulses and two full cycle pulses interspersed with the half cycle pulses. In the sixth block of cycles (Block 6), all full cycle pulses are provided by the microcontroller U1 to triac Q1 so that full power is provided to the external electrical device by the circuit.

Figure 6C:
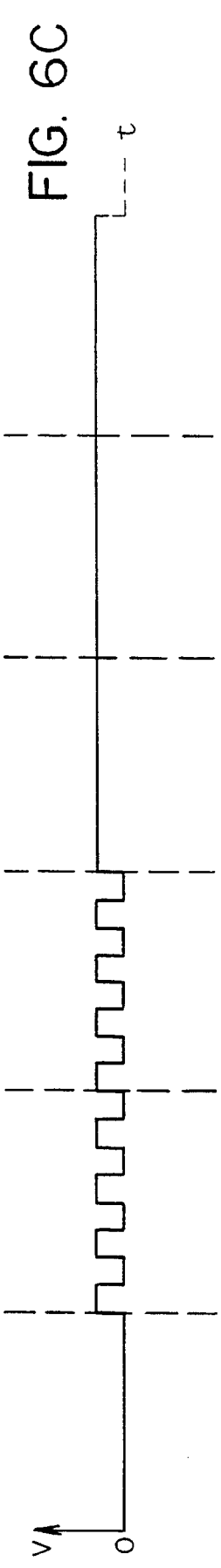

FIG. 6C depicts an example of the waveform of the microcontroller output signal to the power switching circuit 20, where the heater or other electrical device is powered up in two steps. As with FIG. 6B, FIG. 6C is shown with the pulses of the microcontroller output signal in alignment with the blocks of cycles of the AC line voltage shown in FIG. 6A; however, it should be realized that these pulses from the microcontroller U1 need not be in perfect alignment with the zero crossing of the AC line voltage, but rather are timed to occur so that the triac Q1 switches power to the heater or other electrical device preferably at the zero crossing of the AC line voltage.

As shown in FIG. 6C, the microcontroller U1 provides no pulses to trigger triac Q1 in the first block of cycles (Block 1), but when it receives a signal from the comparator U2 that the temperature has fallen below the set point, the microcontroller begins to generate a plurality of half cycle pulses to the triac in the second and third block of cycles (Blocks 2 and 3). The triac Q1, in response to these pulses, provides half the power to the heater by switching the AC voltage to the heater at the zero crossing of the AC voltage.

Following the plurality of half cycle pulses, the microcontroller U1 now provides a plurality of full cycle pulses (which appear as a steady voltage in FIG. 6C) to the triac for the blocks of cycles which follow (Blocks 4, 5, 6 and so forth). Now, full power is provided to the heater by triac Q1.

It should be noted further that the microcontroller U1 of the humidity control device may be programmed in the same manner described above with respect to the temperature control device of the present invention to gradually power up or down a dehumidifier, heater or the like as described previously.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A humidity control device for sensing humidity and for selectively energizing an electrical device connected to an AC line voltage in response to the sensed humidity, which comprises:

a humidity sensing circuit, the humidity sensing circuit including circuit components, at least one of the circuit components being a humidity sensor which is coupled and responsive to the AC line voltage, the circuit components forming a balanced circuit such that the humidity sensing circuit is substantially self-compensating for AC line voltage variations, the humidity sensing circuit sensing the humidity and comparing the sensed humidity with a preselected humidity set point and generating a first output signal in response to the comparison thereof, a zero crossing detector, the zero crossing detector detecting a zero crossing of the AC line voltage, the zero crossing detector being responsive to the AC line voltage and generating a second output signal indicating the zero crossing thereof, a microcontroller, the microcontroller being responsive to the first and second output signals of the humidity sensing circuit and zero crossing detector and generating a third output signal in response thereto; and means for switching the AC line voltage connected to the electrical device, the AC line voltage switching means being responsive to the third output signal of the microcontroller and selectively providing the AC line voltage to the electrical device in response thereto thereby selectively energizing and deenergizing the electrical device in a manner which substantially reduces radio frequency interference.

2. A humidity control device as defined by claim 1, wherein the humidity sensing circuit includes a first electrical path having a first overall electrical resistance, a second electrical path having a second overall electrical resistance, and a voltage comparator, the second electrical path including the humidity sensor, the humidity sensor having a sensor resistance which varies with the sensed humidity, the second overall electrical resistance of the second electrical path including the sensor resistance, the first and second overall electrical resistances respectively of the first and second electrical paths being substantially equal at a particular humidity sensed by the humidity sensor, each of the first and second electrical paths being provided with at least a portion of the AC line voltage to cause a voltage drop across the first and second overall electrical resistances, the comparator being responsive to the voltage drops across the first and second overall electrical resistances respectively of the first and second electrical paths and generating the first output signal in response thereto.

3. A humidity control device as defined by claim 2, wherein at least one of the first and second electrical paths includes means for compensating for temperature variations, the temperature variation compensating means having a resistance which varies with changes in temperature.

4. A humidity control device as defined by claim 1, wherein the humidity sensing circuit includes a comparator, the comparator having at least first and second inputs, the first input having a reference signal provided thereto, the reference signal corresponding to a preselected humidity set point, the second input having a humidity varying signal provided thereto, the humidity varying signal being responsive to changes in the humidity sensed by the humidity sensor and varying in response thereto, the comparator comparing the reference signal with the humidity varying signal and generating the first output signal in response to the comparison thereof.

5. A humidity control device as defined by claim 1, wherein the humidity sensing circuit includes a first resistor divider network and a second resistor divider network, at least a portion of the first and second resistor divider networks being provided with at least a portion of the AC line voltage and respectively generating first and second voltage drops in response thereto, the second resistor divider network including the humidity sensor, the humidity sensor having a sensor resistance which varies in response to the humidity sensed by the humidity sensor; and wherein the humidity sensing circuit further includes a voltage comparator, the voltage comparator being responsive to a comparison of the first and second voltage drops respectively generated by the first and second resistor divider networks and generating the first output signal in response to the comparison thereof.

6. A humidity control device as defined by claim 1, wherein at least a portion of the AC line voltage is provided to the humidity sensing circuit, and wherein the humidity sensor is an AC resistive type humidity sensor.

7. A humidity control device as defined by claim 6, wherein the humidity sensing circuit includes a comparator, the comparator having at least first and second inputs, the first input having a reference signal provided thereto, the reference signal corresponding to a preselected humidity set point, the second input having a humidity varying signal provided thereto, the humidity varying signal being responsive to changes in the humidity sensed by the humidity sensor and varying in response thereto, the comparator comparing the reference signal with the humidity varying signal and generating the first output signal in response to the comparison thereof.

8. A humidity control device as defined by claim 1, wherein the humidity sensing circuit includes:
   a first resistor divider network, the first resistor divider network being provided with at least a portion of the AC line voltage and generating a first AC voltage drop in response thereto;
   a second resistor divider network, the second resistor divider network being provided with the at least portion of the AC line voltage and generating a second AC voltage drop in response thereto, the second resistor divider network including the humidity sensor, the humidity sensor being an AC resistive type sensor, the second AC voltage drop being at least partially across the humidity sensor;
   means responsive to the first AC voltage drop for generating a first DC voltage in response thereto, the first DC voltage being proportional to the first AC voltage drop and corresponding to a preselected humidity set point;
   means responsive to the second AC voltage drop for generating a second DC voltage in response thereto, the second DC voltage being proportional to the second AC voltage drop and varying with the humidity sensed by the humidity sensor; and
   a voltage comparator, the voltage comparator comparing the first DC voltage and the second DC voltage and generating the first output signal in response to the comparison thereof.

9. A humidity control device as defined by claim 8, wherein at least one of the first and second resistor divider networks includes means for compensating for temperature variations, the temperature variation compensating means having a resistance which varies with changes in temperature.

10. A control device for one of providing power gradually to and removing power gradually from an electrical device connected to an AC voltage, which comprises:
    means for determining when power is to be applied to the electrical device, the power determining means generating a first output signal indicative thereof;
    a zero crossing detector, the zero crossing detector detecting a zero crossing of the AC voltage, the zero crossing detector being responsive to the AC voltage and generating a second output signal indicating the zero crossing thereof;
    a microcontroller, the microcontroller being responsive to the first output signal of the power determining means and the second output signal of the zero crossing detector and generating a third output signal in response thereto; and
    means for switching the AC voltage connected to the electrical device, the AC voltage switching means being responsive to the third output signal of the microcontroller and selectively providing the AC voltage to the electrical device in response thereto thereby selectively energizing and deenergizing the electrical device;
    the third output signal of the microcontroller being in the form of electrical pulses of voltage timed to selectively switch on and off the AC voltage switching means for half cycles and full cycles over a predetermined number of cycles of the AC voltage provided to the electrical device.

11. A control device for one of providing power gradually to and removing power gradually from an electrical device connected to an AC voltage, which comprises:
    a zero crossing detector, the zero crossing detector detecting a zero crossing of the AC voltage, the zero crossing detector being responsive to the AC voltage and generating a first output signal indicating the zero crossing thereof;
    a microcontroller, the microcontroller being responsive to the first output signal of the zero crossing detector and generating a second output signal in response thereto; and
    means for switching the AC voltage connected to the electrical device, the AC voltage switching means being responsive to the second output signal of the microcontroller and selectively providing the AC voltage to the electrical device in response thereto thereby selectively energizing and deenergizing the electrical device;
    the second output signal of the microcontroller being in the form of electrical pulses timed to selectively switch on and off the AC voltage switching means for half cycles and full cycles over a predetermined number of cycles of the AC voltage provided to the electrical device.

12. A control device as defined by claim 11, wherein the second output signal of the microcontroller includes:
    a first plurality of electrical pulses, each electrical pulse of the first plurality of electrical pulses having a first pulse width equal to about one half cycle of the AC line voltage and being periodically spaced apart from each other; and
    a second plurality of electrical pulses, the second plurality of electrical pulses following the first plurality of electrical pulses, each electrical pulse of the second plurality of electrical pulses having a second pulse width equal to about a full cycle of the AC line voltage and being periodically spaced apart;
    wherein the first plurality of electrical pulses selectively switches on and off the AC switching means for half cycles of the AC voltage provided to the electrical device; and
    wherein the second plurality of electrical pulses selectively switches on and off the AC switching means for full cycles of the AC voltage provided to the electrical device.

13. A control device for providing power gradually to an electrical device connected to an AC voltage, which comprises:
    a zero crossing detector, the zero crossing detector detecting a zero crossing of the AC voltage, the zero crossing detector being responsive to the AC voltage and generating a first output signal indicating the zero crossing thereof;

a microcontroller, the microcontroller being responsive to the first output signal of the zero crossing detector and generating a second output signal in response thereto; and means for switching the AC voltage connected to the electrical device, the AC voltage switching means being responsive to the second output signal of the microcontroller and selectively providing the AC voltage to the electrical device in response thereto thereby selectively energizing and deenergizing the electrical device;

the second output signal of the microcontroller being in the form of electrical pulses timed to selectively switch on and off the AC switching means for half cycles and full cycles of the AC voltage provided to the electrical device, wherein the second output signal of the microcontroller includes a first plurality of electrical pulses having a first pulse width and a second plurality of electrical pulses having a second pulse width, the first pulse width being equal to about one half cycle of the AC voltage and the second pulse width being equal to about a full cycle of the AC voltage, at least some of the electrical pulses of the second plurality of electrical pulses being interspersed with at least some of the electrical pulses of the first plurality of electrical pulses over a predetermined number of cycles of the AC voltage.

14. A method of one of providing an AC voltage gradually to and removing an AC voltage gradually from an electrical device selectively connected to an AC voltage source, which comprises the steps of:

generating a first plurality of electrical pulses and a second plurality of electrical pulses, each of the electrical pulses of the first plurality of electrical pulses having a first pulse width equal to about one half cycle of the AC voltage, each of the electrical pulses of the second plurality of electrical pulses being equal to about one full cycle of the AC voltage;

arranging the first and second pluralities of electrical pulses such that the first plurality of electrical pulses precede the second plurality of electrical pulses over a predetermined number of cycles of the AC voltage when providing power gradually to the electrical device and follow the second plurality of electrical pulses over a predetermined number of cycles of the AC voltage when removing power gradually from the electrical device; and selectively switching the AC voltage provided to the electrical device in response to the first and second pluralities of electrical pulses thereby selectively energizing and deenergizing the electrical device.

15. A method as defined by claim 14, which comprises the further step of:

detecting the zero crossing of the AC voltage; and timing the occurrence of the electrical pulses of the first and second pluralities of electrical pulses such that the AC voltage provided to the electrical device is selectively switched in response to the first and second pluralities of electrical pulses at the zero crossing of the AC voltage.

16. A method of providing an AC voltage gradually to an electrical device selectively connected to an AC voltage source, which comprises the steps of:

generating a first plurality of electrical pulses and a second plurality of electrical pulses, each of the electrical pulses of the first plurality of electrical pulses having a first pulse width equal to about one half cycle of the AC voltage, each of the electrical pulses of the second plurality of electrical pulses having a second pulse width equal to about one full cycle of the AC voltage;

arranging the first and second pluralities of electrical pulses such that at least some of the electrical pulses of the second plurality of electrical pulses are interspersed with at least some of the electrical pulses of the first plurality of electrical pulses over a predetermined number of cycles of the AC voltage; and selectively switching the AC voltage provided to the electrical device in response to the first and second pluralities of electrical pulses thereby selectively energizing and deenergizing the electrical device.

17. A method as defined by claim 16, which comprises the further steps of:

detecting the zero crossing of the AC voltage; and timing the occurrence of the electrical pulses of the first and second pluralities of electrical pulses such that the AC voltage provided to the electrical device is selectively switched in response to the first and second pluralities of electrical pulses at the zero crossing of the AC voltage.

* * * * *